United States Patent
Luo et al.

(10) Patent No.: US 9,357,150 B2
(45) Date of Patent: May 31, 2016

(54) IMAGE SENSOR WITH INTEGRATED POWER CONSERVATION CONTROL

(71) Applicant: CapsoVision, Inc., Saratoga, CA (US)

(72) Inventors: Jiafu Luo, Irvine, CA (US); Kang-Huai Wang, Saratoga, CA (US)

(73) Assignee: CapsoVision Inc., Saratoga, CA (US)

( * ) Notice: Subject to any disclaimer, the term of this patent is extended or adjusted under 35 U.S.C. 154(b) by 252 days.

(21) Appl. No.: 14/095,092

(22) Filed: Dec. 3, 2013

(65) Prior Publication Data

US 2015/0156434 A1  Jun. 4, 2015

(51) Int. Cl.
| | |
|---|---|
| *H04N 5/378* | (2011.01) |
| *H04N 5/357* | (2011.01) |
| *A61B 5/00* | (2006.01) |
| *A61B 1/00* | (2006.01) |
| *H04N 5/232* | (2006.01) |

(52) U.S. Cl.
CPC ........ *H04N 5/378* (2013.01); *A61B 1/00* (2013.01); *A61B 1/00009* (2013.01); *A61B 1/00025* (2013.01); *A61B 5/0084* (2013.01); *H04N 5/23241* (2013.01); *H04N 5/23245* (2013.01); *H04N 5/357* (2013.01)

(58) Field of Classification Search
CPC ............. H03M 1/002; H01L 27/14643; H01L 27/14601; A61B 1/00; A61B 1/00009; A61B 1/00025; A61B 1/0084; H04N 5/378; H04N 5/357; H04N 5/374; H04N 5/23241; H04N 5/23245
See application file for complete search history.

(56) References Cited

U.S. PATENT DOCUMENTS

| | | | | |
|---|---|---|---|---|
| 2003/0011499 A1* | 1/2003 | Amar | ............... | H03M 1/002 341/155 |
| 2003/0080340 A1* | 5/2003 | Henderson | ........... | H04N 5/3575 257/72 |
| 2004/0046685 A1* | 3/2004 | Yun | ............... | H03M 1/002 341/169 |
| 2005/0258893 A1* | 11/2005 | Garlapati | ............... | H03M 1/002 327/544 |
| 2005/0258991 A1* | 11/2005 | Efland | ............... | H03M 1/002 341/144 |
| 2006/0250510 A1* | 11/2006 | Jacobs | ............... | H04N 5/335 348/294 |
| 2006/0261996 A1* | 11/2006 | Augusto | ............... | H03M 1/125 341/155 |
| 2007/0030190 A1* | 2/2007 | Lee | ............... | H03M 1/002 341/155 |
| 2008/0135895 A1* | 6/2008 | Lee | ............... | H04N 3/155 257/290 |
| 2009/0058700 A1* | 3/2009 | Chen | ............... | H03M 1/002 341/122 |
| 2010/0079202 A1* | 4/2010 | Sugimoto | ............... | H03M 1/002 327/544 |

(Continued)

*Primary Examiner* — John Lee
(74) *Attorney, Agent, or Firm* — Blairtech Solution LLC

(57) ABSTRACT

An integrated image sensor circuit with multiple power modes is disclosed. The integrated circuit comprises a pixel array, an analog block to process analog signal associated with the pixel array, where the analog block comprises an analog to digital convertor (ADC), and a first control circuit to enable/disable the analog block or to configure the analog block to a high/low-power mode depending on whether the pixel array is in a readout frame or in a reset frame with no active readout. The integrated image sensor circuit may further comprise a post-processing block and a second control circuit to enable/disable the post-processing block or to configure the post-processing block to the high-power mode or the low-power mode depending on whether the pixel array is in the readout frame or in the reset frame with no active readout.

22 Claims, 3 Drawing Sheets

(56) References Cited

U.S. PATENT DOCUMENTS

| | | | |
|---|---|---|---|
| 2010/0164777 A1* | 7/2010 | Cui | H03M 1/002 341/145 |
| 2011/0050967 A1* | 3/2011 | Matsumoto | H03M 1/745 348/294 |
| 2012/0038809 A1* | 2/2012 | Lee | H04N 5/3575 348/308 |
| 2012/0097840 A1* | 4/2012 | Kim | H03M 1/002 250/208.1 |
| 2012/0274817 A1 | 11/2012 | Sun | |
| 2013/0076552 A1* | 3/2013 | Nam | H03M 1/002 341/164 |
| 2013/0107091 A1* | 5/2013 | Teshima | H04N 5/365 348/300 |
| 2013/0229293 A1* | 9/2013 | Standley | H03M 1/002 341/122 |
| 2013/0258151 A1 | 10/2013 | Ayers | |
| 2014/0048686 A1 | 2/2014 | Johansson | |
| 2014/0233679 A1* | 8/2014 | Rajagopal | H04L 27/2649 375/340 |
| 2014/0263957 A1 | 9/2014 | Kim | |
| 2015/0008308 A1 | 1/2015 | Huang et al. | |
| 2015/0156434 A1* | 6/2015 | Luo | H04N 5/378 250/208.1 |

\* cited by examiner

IMAGE SENSOR WITH INTEGRATED POWER CONSERVATION CONTROL

FIELD OF THE INVENTION

The present invention relates to integrated image sensor circuits. In particular, the present invention relates to image sensing ICs that use multiple power modes to reduce the power consumption.

BACKGROUND AND RELATED ART

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily inpatient services that involve a significant amount of time from clinicians and thus are costly.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule. The wireless-based capsule camera system will require a patient to wear a wireless transceiver and data recorder to receive and record the captured images. The capsule camera may stay in the body for over ten hours. Therefore, the patient may have to wear the wireless data receiver pack for extended hours which may be uncomfortable.

An autonomous capsule camera system with on-board data storage was disclosed in the U.S. Pat. No. 7,983,458, entitled "In Vivo Autonomous Camera with On-Board Data Storage or Digital Wireless Transmission in Regulatory Approved Band," granted on Jul. 19, 2011. The capsule camera with on-board storage archives the captured images in on-board non-volatile memory. The capsule camera is retrieved upon its exiting from the human body. The images stored in the non-volatile memory of the retrieved capsule camera are then accessed through an output port on in the capsule camera. The images can be processed and displayed on viewing station and examined by diagnostician.

The capsule camera system typically consists of an optical lens or lens system, and a light sensing element. The light sensing element is based on integrated-circuit sensor fabricated through various manufacturing process, such as CMOS (complementary metal-oxide semiconductor) or CCD (charge-coupled device) processes. CMOS image sensors are becoming more popular and have been used extensively today in various digital imaging applications. The light sensing devices traditionally have light sensing elements, called pixels, arranged into one-dimensional (one row) or two-dimensional (many rows and columns) arrays. The pixel array is aligned with the image formed by the associated optical lens system and positioned within the focus depth of the optical system. Each pixel provides an electrical output corresponding to the incident light to which the pixel is exposed.

For the capsule camera application, the capsule device has to travel in the human body for an extended period of time. Furthermore, the capsule device usually is powered by batteries. During the course of imaging the gastrointestinal track inside the human body, a capsule camera may have to capture tens of thousands of images. The image sensor is one of the major power consuming devices. Therefore, power consumption of such CMOS image sensors is an important factor that limits the lifetime of such system, if the image sensor is powered by disposable batteries. If it is powered by rechargeable batteries, the power consumption will determine the usage time between two charges. As a result, it is desirable to reduce the power consumption of the image sensor.

A capsule camera system typically consists of one or more CMOS image sensors, LED light sources, image processing ASIC (application specific integrated circuit) and other components. In order to keep the capsule camera easily swallowable, the physical size of the capsule camera becomes very limited. As a result, the batteries are usually very small and the power consumption of all components inside the capsule camera, including the image sensor becomes a critical issue. Therefore, it is desirable to develop an image sensor with power saving control to extend the battery life.

BRIEF SUMMARY OF THE INVENTION

An integrated image sensor circuit with multiple power modes is disclosed. According to embodiments of the present invention, the integrated circuit comprises a pixel array to capture an image projected thereon; an analog block to process analog signal associated with the pixel array, where the analog block comprises an analog to digital convertor (ADC); and a first control circuit to enable or disable the analog block or to configure the analog block to a high-power mode or a low-power mode depending on whether the pixel array is in a readout frame or in a reset frame with no active readout. The reset frame corresponds to a period of time starting from a global reset to immediately before a first-row readout for the integrated image sensor circuit operated in a global shutter mode. The reset frame corresponds to a period of time starting from a first-row reset to immediately before the first-row readout for the integrated image sensor circuit operated in a rolling shutter mode.

According to one embodiment, the analog block is enabled or is configured to the high-power mode when the pixel array is in the readout frame, and the analog block is disabled or is configured to the low-power mode when the pixel array is in the reset frame with no active readout. In another embodiment, the analog block is powered up at a short period before the readout frame starts, and the short period depends on a settling time associated with said at least one analog block. The short period may have a range as small as one order of microsecond or a range as large as one order of millisecond. The analog block may further comprise a bias circuit, a reference circuit, a gain amplifier or any combination. In one embodiment, the analog block is powered down once the readout frame is completed.

In another embodiment, the integrated image sensor circuit further comprises a post-processing block and a second control circuit to enable or disable the post-processing block or to configure the post-processing block to the high-power mode or the low-power mode depending on whether the pixel array is in the readout frame or in the reset frame with no active readout. The post-processing block can be enabled or be configured to the high-power mode when the pixel array is in the readout frame. The post-processing block can be disabled or be configured to the low-power mode when the pixel array is in the reset frame with no active readout. The post-processing block can be powered up at a short period before the readout frame starts, where the short period depends on a settling time associated with the post-processing block and wherein the settling time associated with the post-processing block is shorted than the settling time associated with the analog block. The analog block and the post-processing block are powered down once the readout frame is completed. The post-processing block may further comprise noise reduction, demosaicing, edge sharpening, color format conversion or any combination.

In yet another embodiment, the integrated image sensor circuit further comprises a configurable timing circuit and a third control circuit to configure the configurable timing circuit to provide a high clock frequency or a low clock frequency for the integrated image sensor circuit depending on whether the pixel array is in the readout frame or in the reset frame with no active readout. The configurable timing circuit is configured to provide the high clock frequency when the pixel array is in the readout frame, and the configurable timing circuit is configured to provide the low clock frequency when the pixel array is in the reset frame with no active readout.

The integrated image sensor circuit may further comprise a regulator and a fourth control circuit to configure the regulator to provide a high-current output or a low-current output depending on whether the pixel array is in the readout frame or in the reset frame with no active readout. The regulator incurs higher quiescent current when the regulator is configured to provide the high-current output. The regulator can be configured to provide the high-current output when the pixel array is in the readout frame and the regulator can be configured to provide the low-current output when the pixel array is in the reset frame with no active readout.

DETAILED DESCRIPTION OF THE INVENTION

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Figure 1:
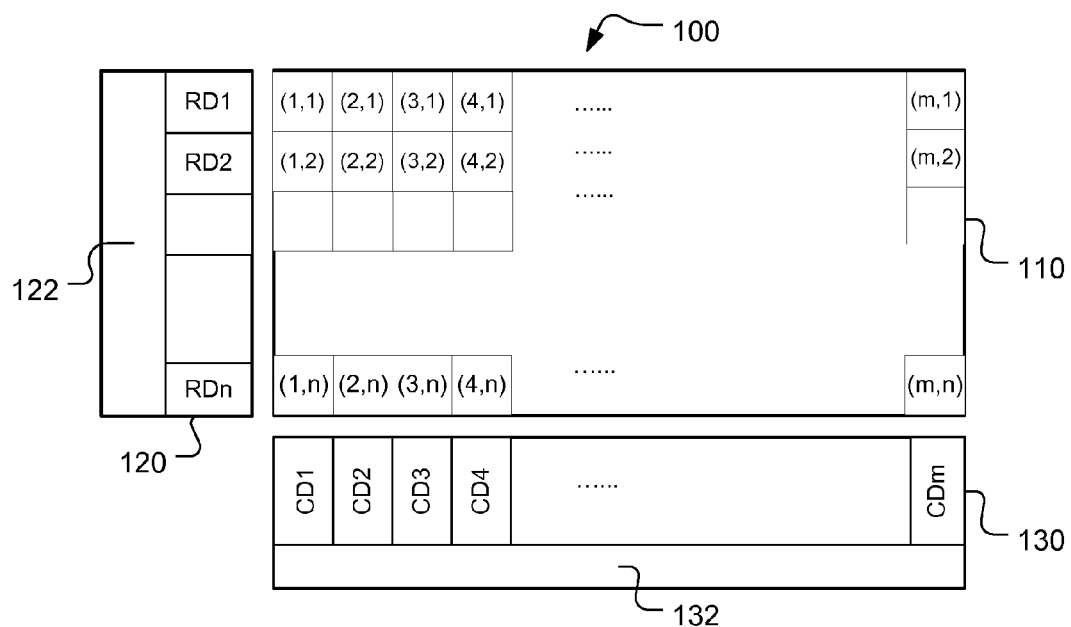
FIG. 1 illustrates an exemplary layout of a two-dimensional pixel array with supporting column and row driving circuits.

A conventional digital camera typically has an optical imaging path with an image sensing IC comprising a two-dimensional (2-D) pixel array. The image sensor is placed at or near the focal plane of the optical imaging path, with the center of the 2-D pixel array aligned with the center of the optical imaging path. FIG. 1 illustrates a typical image sensor 100 including a 2-D pixel array 110, row driver circuit 120 and column driver circuit 130. The 2-D pixel array 100 is configured as two-dimensional sensing elements with n rows and m columns. Each row is substantially the same. If the pixel array is used as a color sensor, a color filter with different patterns may be applied on top of the pixel array. The pixel locations of the 2-D array are designated as (x,y), where x represents the horizontal position and y represents the vertical position. The coordinates x and y also represent the column and row numbers of the 2-D pixel array respectively. While FIG. 1 illustrates an example where the pixels in all rows are vertically aligned, some pixel arrays may have offset patterns from row to row. For example, a pixel array may have half-pixel offset for every other row.

In the horizontal direction, pixels in the same row share common electrical signals provided by row driver 120. Row driver 120 consists of individual row driving circuits RD1, RD2, ..., RDn for corresponding n rows of the pixel array. In addition to individual row driving circuits, row driver 120 also includes common components 122 that support all individual row driving circuits. Similarly, pixels in the same column share certain common electrical signals, provided by column circuit 130. Column circuit 130 consists of common components 132 and individual column driving circuits, CD1, CD2, ..., CDm for corresponding m columns of the pixel array.

Figure 2:
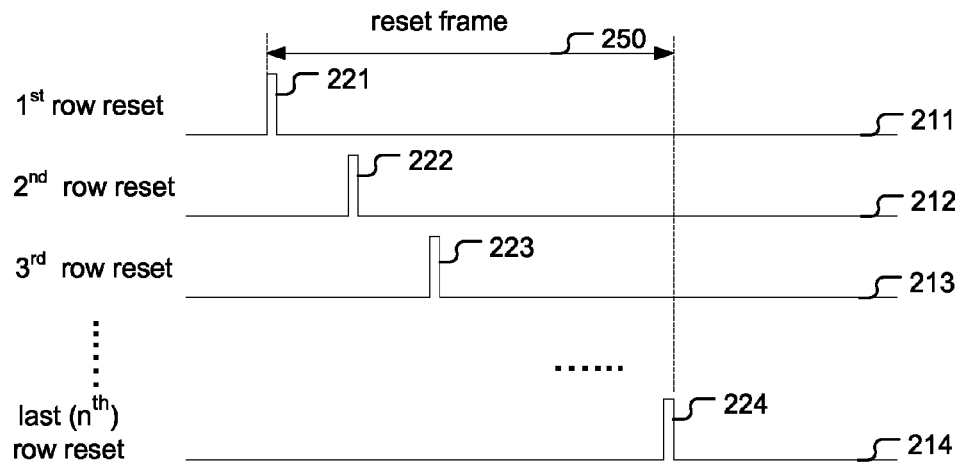
FIG. 2 illustrates exemplary timing diagrams to operate a two-dimensional pixel array.
Figure 2:
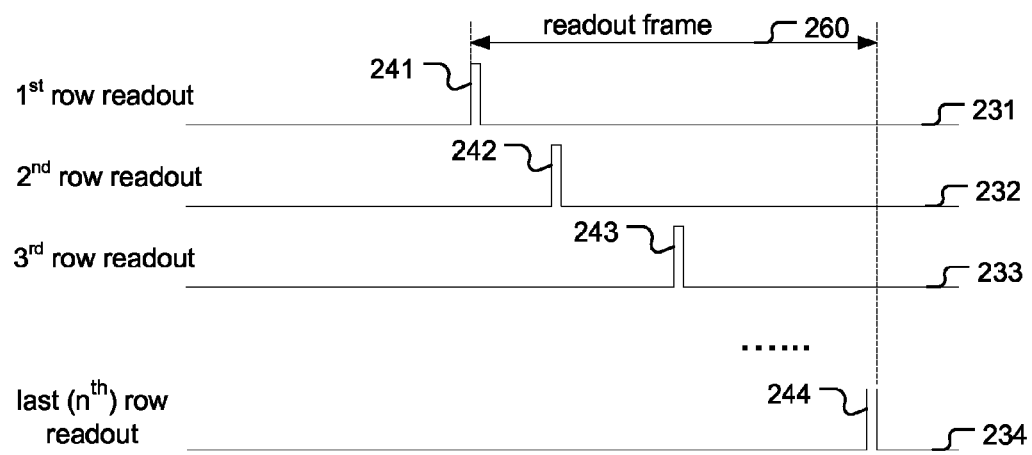

FIG. 2 illustrates exemplary timing diagrams to operate the 2-D pixel array 100 in FIG. 1. To operate the pixel array, the pixel rows are reset before charges are accumulated and read out from the sensing elements. The reset signals 211, 212, 213 and 214 are shown for rows 1, 2, 3 and n respectively. Individual row driving circuits generate the respective reset signals. For example, reset signal 211 is generated by the row driving circuit RD1 for the 1$^{st}$ row. In the instance as indicated by a short high signal (221, the reset pulse), the 1$^{st}$ row is reset and the row of pixels will start integrating light signals. Individual row driving circuit RD2 for the 2$^{nd}$ row generates timing signal 212, which comprises a reset pulse indicated by 222 to reset the 2$^{nd}$ row. The time difference between signal 221 and signal 222 corresponds to one line period. Similarly, timing signal 213 is generated by individual row driving circuit RD3 for the 3$^{rd}$ row and the reset pulse 223 is one line period behind the reset pulse 222. This continues for the remaining rows of the pixel array until the last row is reset. While a pulse signal is illustrated in FIG. 2 to cause a corresponding row to reset, other signal types may also be used. For example, an upward transient signal, such as the leading edge of a positive pulse, or a downward transient signal, such as the trailing edge of a positive pulse may also be used to trigger the reset.

After a period of charge accumulation time, the charge signals can be read out from the pixel array in a row by row fashion. As mentioned before, the sensing elements start to accumulate charges caused by the incident light ray after the reset pulse. FIG. 2 illustrates the readout signals generated by the individual driving circuits. For example, individual row driving circuit RD1 for 1$^{st}$ row generates a timing signal 231, which comprises a readout pulse 241 to trigger the readout for the 1$^{st}$ row. The readout pulse occurs at a desired instance after the reset pulse 221 for the 1$^{st}$ row to integrate charges. Readout pulses 242 and 243 of readout signal 232 and 233 for the 2$^{nd}$ row and the 3$^{rd}$ row occur at one row period after respective readout signals 241 and 242. The readout pulses for the remaining rows continue until all rows are read. Again, while a pulse signal is illustrated in FIG. 2 to cause a corresponding row to start the readout, other signal types may also be used. For example, an upward transient signal, such as the leading edge of a positive pulse, or a downward transient signal, such as the trailing edge of a positive pulse may also be used as the readout signal.

The timing scheme shown in FIG. 2 is referred as rolling shutter operation. For video application, the timing signal shown in FIG. 2 repeats frame after frame to form a stream of image frames, which is also referred as a video sequence. As shown in the timing signals of FIG. 2, each row integrates light signal at slightly different time period using the rolling shutter operation. Two neighboring rows have reset time, charge accumulation time and readout time apart by one line period. The time difference between 1$^{st}$ and last row is about one frame apart, which may be substantial long. Consequently, the resulting picture with fast moving objects may experience the so-called rolling shutter artifact. One manifest of the rolling shutter artifact is that a vertical line becomes a slant line in the captured picture when the vertical line moves quickly horizontally.

The period of time that the pixel array is being reset is referred as reset frame. In the example of rolling shutter operation as shown in FIG. 2, the reset frame corresponds to the period from the first-row reset pulse to the last-row reset pulse. Similarly, the readout frame is defined as the period from the first-row readout pulse to the last-row readout pulse. As shown in FIG. 2, reset frame 250 and readout frame 260 have a certain overlap. The amount of overlap depends on the integration time and total number of readout rows (n). If the integration time is short, 1$^{st}$ row readout pulse 241 occurs at a short time after corresponding reset pulse 221. This will result in larger overlap between reset frame 250 and corresponding readout frame 260. On the other hand, if the integration time is longer, the overlap will become smaller. Once the integration time is longer than n line periods, reset frame 250 and readout frame 260 will have no overlap at all.

While a rolling shutter operation is shown in FIG. 2, other reset schemes, such as global reset, can also be used where all rows will be reset at the same time, instead of row by row sequentially. For sensors operated with the global shutter mode, while the reset frame will be very short, there is still a normal readout frame because the image array needs to be readout one row at a time.

For a typical sensor, during the reset frame and readout frame, different circuits are needed. For example, during readout frame, the whole readout chain will be needed, where the readout chain may include bias and reference circuit, a gain amplifier, an analog to digital convertor (ADC) and output interface. For system-on-chip (SOC) designs, certain digital post-processing may also be performed on outputs from the pixel array during the readout frame. During this time, the sensor will need to run at a clock frequency equal to or higher than the pixel rate. Post-processing for image sensors is known technique in the field. The post-processing may include one or more of the processing techniques selected from a group comprising noise reduction, demosaicing, edge sharpening, and color format conversion.

On the other hand, during the reset frame with no overlapping with the readout frame, most or all of these components of the readout chain and the digital post-processing will not be needed. For simple pixels, only certain timing generators will be needed to drive the row drivers in order to generate reset pulses for each row. Such signals are typically at a much lower frequency compared to the pixel rate. Even for more complex pixels, only a limited amount of analog blocks, such as reference for charge pump circuits, will still be needed. Other components, especially those in the readout chain and any post-processing block, will not be needed. Pixel clock can be turned off during the non-overlapped reset frame to further conserve power.

With the above observation, the power consumption of an image sensor can be reduced by selectively powering down/disabling different on-chip components or selectively configuring on-chip components to different power modes. In one embodiment of the invention, during the reset frame, most or all of the analog blocks and on-chip post-processing blocks will be powered down/disabled or configured to a low-power mode and this will result in substantial power reduction of the image sensor. A very short time before the readout frame starts, these analog blocks will be powered up/enabled or configured to a high-power mode so that the on-chip component can be ready to process pixel output from the sensor array when a readout frame starts. The exact time to power up these blocks in advance depends on the settling time of these analog blocks and can range from a few microseconds to milliseconds. Post-processing digital blocks can be waked up or enabled in a similar manner with slightly different wake-up time since these can typically settle much faster than the analog blocks. Once readout is done, the readout chain analog blocks and post-processing digital blocks can be powered down or disabled again until the pixel array needs to readout again. The terms, high-power mode and low-power mode are relative terms where the high-power mode causes the image sensor to consume more power than the low-power mode. Therefore, the high-power mode may correspond to a normal power mode, while the low-power mode may correspond to a mode using less power than the normal mode.

Furthermore, most CMOS image sensors today include certain amount of digital circuits, even for non-SOC sensors which do not have post-processing circuits. One example is the timing generator that generates different timing pulses for the image sensor. To further reduce the sensor power, such digital blocks can be operated with different clock frequencies, depending on whether the sensor is in the reset frame with no active readout or the readout frame. When the sensor is not in the readout frame, a slower clock can be provided to the digital blocks to reduce power consumption of the digital block. Once the readout frame starts, a faster clock will be sent to the digital block to enable generation of higher frequency signals required for operating the analog readout chain and any post-processing digital block.

In some CMOS sensors, an on-chip regulator is used to provide different current supply capability to power other circuit blocks. This enables some blocks, particularly digital blocks, to operate at different voltages from a single power supply. Quiescent current in a regulator circuit is the current drawn internally, not available to the load. The quiescent current normally is measured as the input current with no load. Accordingly, the quiescent current represents a source of inefficiency of the regulator. Usually, a regulator with capability to supply higher current will incur a higher quiescent current. Therefore, the regulators should match required currents in order to further save power. However, there is usually a trade-off between the quiescent current consumed and the response speed that the regulator can react to load change. According to one embodiment of the present invention, the regulator for image sensors with an on-chip regulator can be operated in at least two different modes. When the sensor is not in a readout frame, the sensor can be operated at a slower clock and any post-processing blocks can be powered down to reduce power consumption. Therefore, there will be very small load and small load change on the power supply generated by the on-chip regulator. In this case, the regulator can be operated in a low-power mode or a low-current regulator is used, where the quiescent current is small. Once the sensor enters the readout frame, larger current will be needed from the regulator. In this case, the regulator is operated in higher power mode or a large-current regulator is used. Accordingly, the power consumption of the CMOS image sensor can be further reduced.

The present invention for reducing image sensor power consumption can be applied to a general sensor where the reset frame and the readout frame may overlap. However, particular care must be taken into consideration during design and layout of an integrated image sensor, especially for the column drive circuitry. A large amount of power change may occur when a sensor enters a readout frame. This large power change can cause large perturbation on the sensor IC. Since image sensors are very sensitive to such perturbations, row offset may become visible in the captured image data. Row noise correction design can be implemented to reduce such effect.

Figure 3:
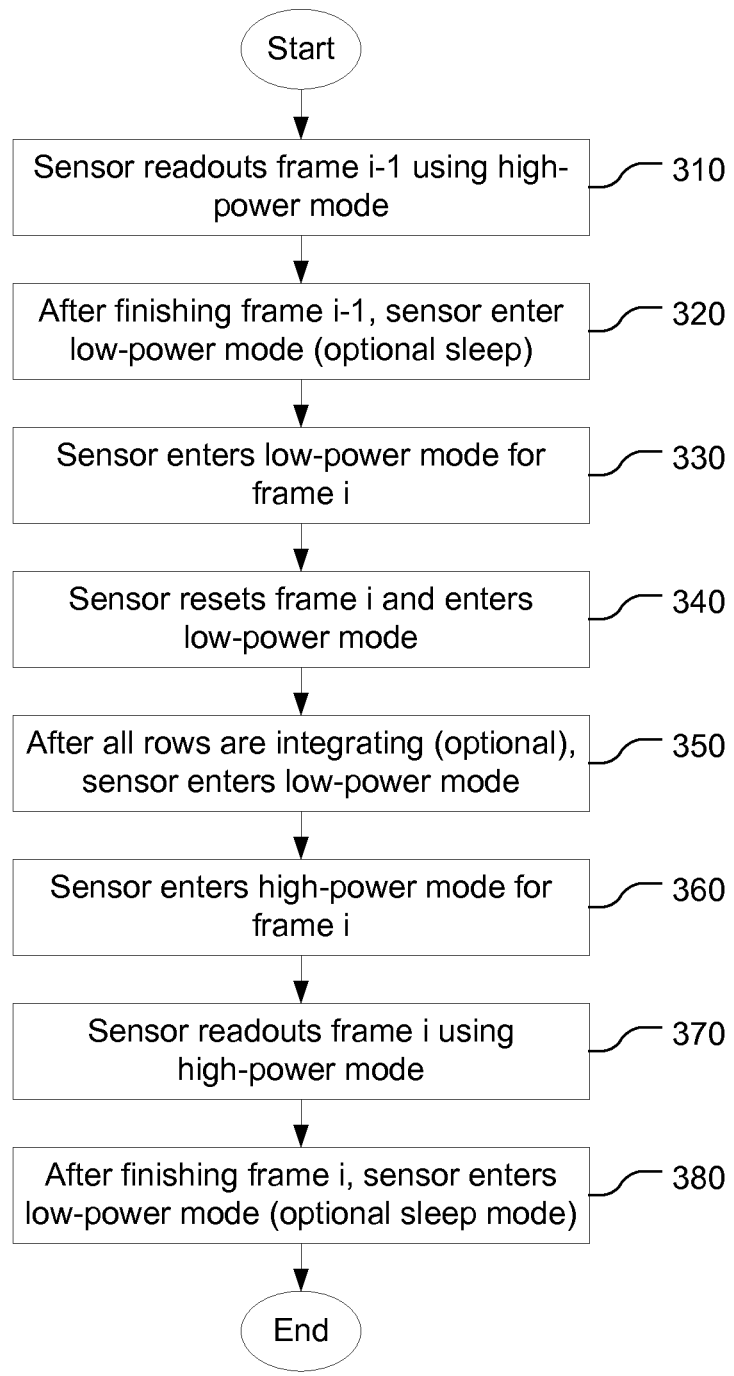
FIG. 3 illustrates an exemplary operational flow chart for an integrated image sensor circuit incorporating multiple power modes according to an embodiment of the present invention.

The present invention is also useful for a CMOS image sensor that has no overlap between the readout frame and the reset frame. FIG. 3 shows an exemplary sensor configuration during various phases for operating a sensor in the video mode. The time sequence starts from readout frame i-1 using a normal power mode (or a high-power mode) as shown in step 310. In the normal power mode, the sensor is configured as follows:

All analog circuits and post-processing circuits, if any, powered up;
Normal (or high) frequency clocks provided for digital blocks and timing generators; and
On-chip regulators operated with a high-current mode (i.e., higher quiescent current).

Once readout frame i-1 ends, after last row has been readout, the sensor enters a low-power mode as shown in step 320. In the low-power mode, the sensor is configured as follows:

Most analog circuits and post-processing blocks, if any, powered down. Analog circuits needed to support sensor reset kept running;
Lower frequency clocks provided for digital blocks and timing generators; and
On-chip regulators operated with a low-current mode (i.e., low quiescent current).

Optionally, if the sensor is running at low frame rate and there is a non-active time between readout frame i-1 and reset frame i, the sensor can be placed into an even more aggressive power saving mode, such as a sleep mode. In the sleep mode, almost all on-chip blocks can be powered down except for a small block that is needed for accepting a wake-up signal or generating such a signal itself with pre-programmed delay.

When frame i is needed, the sensor is waken up and enters the low-power mode again as shown in step 330. This time period can be as short as a few clock cycles, which is enough for the digital blocks and any necessary analog blocks for the sensor reset to settle. The sensor then enters reset frame i, where the reset starts with the first row, followed by the second row, etc., until the last row, n and then the sensor remains in the low-power mode as shown in step 340.

After last row, n has been reset, all rows of the pixel array will be integrating signals as shown in step 350, and the sensor remains in the low-power mode. Step 350 is optional since a sensor can enter a readout frame quickly. For certain sensors, step 350 may require longer time to allow firing of LED light sources or operation of a mechanical shutter.

When the sensor is almost ready for readout operation for frame i, the sensor enters the normal power mode as shown in step 360. Step 360 should be long enough to allow the powered up analog blocks to settle. The time to settle typically ranges from a few microseconds to a few milliseconds.

Once the analog block settles, the sensor starts readout frame 1. In step 370, it reads out image data from the pixel array, one row at a time. Once all rows have been readout, it enters low-power mode again, or an optional sleep mode as shown in step 380.

In the exemplary sensor operation as shown in FIG. 3, the image sensor can achieve substantially lower average power consumption compared to a similar image sensor running in a conventional operation mode. In the case of a conventional sensor operation, in steps 330 through 370, all analog blocks will be powered up once the image sensor is waken up.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. An integrated image sensor circuit, comprising:
a pixel array to capture an image projected thereon;
at least one analog block to process analog signal associated with the pixel array, wherein said at least one analog block comprises an analog to digital convertor (ADC); and
a first control circuit to enable or disable said at least one analog block depending on whether the pixel array is in a readout frame, or in a reset frame with no active readout, or to configure said at least one analog block to a high-power mode or a low-power mode depending on whether the pixel array is in the readout frame, or in the reset frame with no active readout, wherein the readout frame is substantially the same as a first period from a first-row readout pulse to a last-row readout pulse, and the reset frame is substantially the same as a second period from a first-row reset pulse to a last-row reset pulse.

2. The integrated image sensor circuit of claim 1, wherein said at least one analog block is enabled or is configured to the high-power mode when the pixel array is in the readout frame, and wherein said at least one analog block is disabled or is configured to the low-power mode when the pixel array is in the reset frame.

3. The integrated image sensor circuit of claim 2, wherein said at least one analog block is powered up at a short period before the readout frame starts, and wherein the short period depends on a settling time associated with said at least one analog block.

4. The integrated image sensor circuit of claim 3, wherein the short period has a first range as small as one order of microsecond to a second range as large as one order of millisecond.

5. The integrated image sensor circuit of claim 1, wherein said at least one analog block further comprises one or more additional analog blocks selected from an analog group consisting of a bias circuit, a reference circuit and a gain amplifier.

6. The integrated image sensor circuit of claim 1, wherein the reset frame corresponds to a first period of time starting from a global reset to immediately before a first-row readout for the integrated image sensor circuit operated in a global shutter mode and wherein the reset frame corresponds to a second period of time starting from a first-row reset to immediately before the first-row readout for the integrated image sensor circuit operated in a rolling shutter mode.

7. The integrated image sensor circuit of claim 1, wherein said at least one analog block is powered down once the readout frame is completed.

8. The integrated image sensor circuit of claim 1, further comprising at least one post-processing block, and a second control circuit to enable or disable said at least one post-processing block or to configure said at least one post-processing block to the high-power mode or the low-power mode depending on whether the pixel array is in the readout frame or in the reset frame.

9. The integrated image sensor circuit of claim 8, wherein said at least one post-processing block is enabled or is configured to the high-power mode when the pixel array is in the readout frame, and wherein said at least one post-processing block is disabled or is configured to the low-power mode when the pixel array is in the reset frame.

10. The integrated image sensor circuit of claim 9, wherein said at least one post-processing block is powered up at a short period before the readout frame starts, wherein the short period depends on a settling time associated with said at least one post-processing block and wherein the settling time associated with said at least one post-processing block is shorted than a second settling time associated with said at least one analog block.

11. The integrated image sensor circuit of claim 9, wherein said at least one analog block and said at least one post-processing block are powered down once the readout frame is completed.

12. The integrated image sensor circuit of claim 8, wherein said at least one post-processing block further comprises one or more additional post-processing blocks selected from a post-processing group consisting of noise reduction, demosaicing, edge sharpening and color format conversion.

13. The integrated image sensor circuit of claim 1, further comprising a configurable timing circuit and a third control circuit to configure the configurable timing circuit to provide a high clock frequency or a low clock frequency for the integrated image sensor circuit depending on whether the pixel array is in the readout frame or in the reset frame.

14. The integrated image sensor circuit of claim 13, wherein the configurable timing circuit is configured to provide the high clock frequency when the pixel array is in the readout frame, and the configurable timing circuit is configured to provide the low clock frequency when the pixel array is in the reset frame.

15. The integrated image sensor circuit of claim 13, further comprising at least one post-processing block, wherein the configurable timing circuit is configured to provide the high clock frequency and said at least one post-processing block is enabled or is configured to the high-power mode when the pixel array is in the readout frame, and wherein the configurable timing circuit is configured to provide the low clock frequency and said at least one post-processing block is disabled or is configured to the low-power mode when the pixel array is in the reset frame.

16. The integrated image sensor circuit of claim 1, further comprising a regulator and a fourth control circuit to configure the regulator to provide a high-current output or a low-current output depending on whether the pixel array is in the readout frame or in the reset frame, wherein the regulator incurs higher quiescent current when the regulator is configured to provide the high-current output.

17. The integrated image sensor circuit of claim 16, wherein the regulator is configured to provide the high-current output when the pixel array is in the readout frame, and wherein the regulator is configured to provide the low-current output when the pixel array is in the reset frame.

18. The integrated image sensor circuit of claim 16, further comprising at least one post-processing block, wherein the regulator is configured to provide the high-current output and said at least one post-processing block is enabled or is configured to the high-power mode when the pixel array is in the readout frame, and wherein the regulator is configured to provide the low-current output and said at least one post-processing block is disabled or is configured to the low-power mode when the pixel array is in the reset frame.

19. The integrated image sensor circuit of claim 16, further comprising a configurable timing circuit, wherein the regulator is configured to provide the high-current output and the configurable timing circuit is configured to a high clock frequency when the pixel array is in the readout frame, and wherein the regulator is configured to provide the low-current output and the configurable timing circuit is configured to a low clock frequency when the pixel array is in the reset frame.

20. The integrated image sensor circuit of claim 19, further comprising at least one post-processing block, wherein said at least one post-processing block are enabled or is configured to the high-power mode when the pixel array is in the readout frame, and said at least one post-processing block is disabled or is configured to the low-power mode when the pixel array is in the reset frame.

21. The integrated image sensor circuit of claim 1, wherein the integrated image sensor circuit enters the low-power mode or a sleep mode for at least a part of a period between a current readout frame and a next reset frame.

22. The integrated image sensor circuit of claim 21, wherein the integrated image sensor circuit is waken up to a low-power mode when a next frame is needed.

\* \* \* \* \*